United States Patent [19]

Shibata et al.

[11] Patent Number: 5,124,156
[45] Date of Patent: Jun. 23, 1992

[54] CHEWING GUM FOR PREVENTING PYORRHEA ALVEOLARIS

[75] Inventors: Masaki Shibata, Tokyo; Toshio Takiguchi, Urawa; Yoji Saeki, Omiya; Hajime Nunome, Tsukui, all of Japan

[73] Assignee: Lotte Company Limited, Tokyo, Japan

[21] Appl. No.: 570,956

[22] Filed: Aug. 20, 1990

[30] Foreign Application Priority Data

Aug. 25, 1989 [JP] Japan .................. 1-217572

[51] Int. Cl.⁵ .............................................. A61K 9/68
[52] U.S. Cl. ................................... 424/440; 424/48; 424/50; 424/58; 426/3
[58] Field of Search ............... 424/440, 48, 50, 58; 426/3

[56] References Cited

U.S. PATENT DOCUMENTS

| | | | |
|---|---|---|---|
| 1,460,179 | 6/1923 | Ruthrauff | 424/50 |
| 3,171,782 | 3/1965 | Fellonneau | 424/48 |
| 3,242,056 | 3/1966 | DuBois-Prevost | 424/50 |
| 4,612,190 | 9/1986 | Sato | 424/49 |
| 4,842,846 | 6/1989 | Nakano | 424/50 |

Primary Examiner—Thurman K. Page
Assistant Examiner—D. Gabrielle Phelan
Attorney, Agent, or Firm—Young & Thompson

[57] ABSTRACT

A chewing gum for preventing pyorrhea alveolaris contains 0.2 to 3.0% of lysozyme of egg white and 0.05 to 0.5% of mace extract.

1 Claim, No Drawings

CHEWING GUM FOR PREVENTING PYORRHEA ALVEOLARIS

FIELD OF THE INVENTION

The present invention relates to a chewing gum which is effective to prevent pyorrhea (gingivitis), and in particular relates to a chewing gum with which pyorrhea alveolaris may be effectively prevented, or restricted by formulating a combination of distinct natural active ingredients as a chewing gum.

BACKGROUND OF THE INVENTION

The pyorrhea alveolaris is one of typical dental diseases as well as dental caries, and is not a disease of a tooth itself but rather is a chronic disease which occurs in peripheral tissues for, supporting a tooth, in which the alveolar bone which is a part of the jaw bone is absorbed and destroyed, and a series of tissues which connects the bone and the tooth is destroyed to produce suppuration. Consequently, such symptoms are finally shown in many cases that pus appears and the tooth becomes unsteady. As initial symptoms, an itching sensation of the gums (tissue), hemorrhaging and the like take place.

As the cause of pyorrhea alveolaris are listed many ones, among which such a case is considered to be dominant as particularly important one that an inflammation is caused by stimulation to the gums due to the tartar formed by depositing of lime salts in the saliva on dental plaques stuck on the tooth, to which suppuration bacteria infect to produce pyorrhea alveolaris. Namely, as in the case of dental caries, it is considered also in the falling ill and the proceeding process of pyorrhea alveolaris that infection by bacteria is an important factor.

Some trials have been done in which attention is given to the relation between infectious microorganisms and diseases of the oral cavity such as pyorrhea alveolaris, and the growth of infectious microorganisms is restricted or inhibited, thereby prevention or restriction of such diseases of the oral cavity is intended to follow.

When the growth of infectious microorganisms is intended to be restricted or inhibited in the oral cavity, for example, by using some active substance, it is desirable for the active substance to satisfy such conditions that it has no toxicity, it has an effective activity against microorganisms, it has no taste or odor or has good taste, it can easily be used in a relatively small amount, it has good stability, it is advantageous from a view of cost and the like. According to these viewpoints, it has been carried out in order to prevent or restrict diseases of the oral cavity such as pyorrhea alveolaris and dental caries, for example, that lysozyme is added to foods such as chewing gums and the like.

Lysozyme exists also in the oral cavity especially as an enzyme of saliva which is known to act against bacteria to destroy it. This is caused owing to the activity of the enzyme to decompose polysaccharide in the bacterial membrane of the bacteria. In addition, lysozyme is known to have the anti-bacterial action as well as the anti-viral action, the hemostasis action, the anti-inflammatory action and the like.

As one of trials for applying lysozyme to compositions for the oral cavity can be exemplified a production method of a chewing gum composition for preventing pyorrhea alveolaris and dental caries which has been disclosed by the present applicant in the Japanese Patent Publication No. 49-32066. In this publication the present applicant has disclosed a production method of a chewing gum composition for preventing pyorrhea alveolaris and dental caries characterized in that a chewing gum base obtained by a usual means is heated to not more than 60° C., to which a chewing gum additive is added to mix by kneading, and lysozyme is added so as to be contained by 1 to 60 mg units per one g of a chewing gum product.

The chewing gum composition obtained according to this technology is sufficiently effective to prevent pyorrhea alveolaris and dental caries, while as the result of further investigation of the present inventors, it has been found that a distinct natural active ingredient is formulated in combination with lysozyme as a chewing gum, thereby a chewing gum which may more effectively prevent or restrict especially pyorrhea alveolaris can be realized to complete the present invention.

SUMMARY OF THE INVENTION

The object of the present invention is to provide a chewing gum which may more effectively prevent or restrict especially pyorrhea alveolaris by formulating lysozyme as a chewing gum in combination with a distinct active ingredient which satisfies such conditions that it has no toxicity, it has an effective activity against microorganisms, it has no taste or ordor or has good taste, it can easily be used in a relatively small amount, it has good stability, it is advantageous from a view of cost and the like.

According to the present invention, there is provided a chewing gum for preventing pyorrhea alveolaris which contains 0.2 to 3.0% by weight of lysozyme of egg white and 0.05 to 0.5% by weight of mace extract.

PREFERRED EMBODIMENT OF THE INVENTION

Lysozyme is an enzyme which hydrolyzes $\beta$-1,4-bond between residues of N-acetylmuramic acid and 2-acetylamino-2-deoxy-D-glucose in mucopolysaccharides, mucopeptides, or chitins, which is contained in the pancreas, the white of an egg, mucus, plant latexes and the like. Among them, the lysozyme of egg white has a molecular weight of 14400, which comprises one polypeptide chain comprising 129 amino acid residues, contains four —S—S— linkage in the molecule, and is one of enzyme proteins the amino acid sequences of which have been completely determined.

In the present form of the lysozyme of egg white may be used, for example, a crystalline egg white lysozyme may be used.

The mace is peel of seeds of a plant of Myristicaceae, *Myristica fragrans Houttuyn*, which is produced in Sumatra Indonesia, East Africa, Ceylon, India and the like. An extract thereof is the mace extract, which is produced by drying the peel of seeds to make powder, and generally to obtain 1 kg of the mace is necessary not less than 400 kg of nutmeg. As commercially available products are one contained in a can (1 kg and 10 kg) and one contained in a wood box under the trade name of Spice (Kenda) Mace and the like, and one in any form may be used for the chewing gum for preventing pyorrhea alveolaris of the present invention.

The mace is generally used as spices and coloring agents, which gives distinct and exotic flavor when added to butter of ginger breads or used for pound cakes and chocolates, and it is also used for pickles, soup, sauce and the like, which is used for food processing in many cases in Japan.

The mace has strong perfume, the essential oil component of which has a function to extinguish disagreeable odors of foods, providing a gold color and having anti-oxidation activity. In the outer peel of seeds of nutmeg flower is contained 4 to 9% of perfume oil, main components of which are α-pinene, β-pinene, and myristin, and the essential oil component is considered to comprise α-pinene, β-pinene, 80% of d-camphene, 8% of dipentene, linalool, 6% of geraniol, 40% of myristin, eugenol, isoeugenol, $C_1$ to $C_{14}$ fatty acids and esters thereof.

The chewing gum for preventing pyorrhea alveolaris according to the present invention thus contains 0.2 to 3.0% by weight of lysozyme of egg white and 0.05 to 0.5% by weight of mace extract.

In case of more than 0.5% of mace extract or in case of more than 3.0% of lysozyme of egg white, considerably bad influence on taste is given, so that the upper limit of the contents should be established as hereinbefore described.

In case of less than 0.05% of mace extract or in case of less than 0.2% of lysozyme of egg white, effect on pyorrhea alveolaris is insufficient, so that the lower limit of the contents should be established as hereinbefore described.

It is preferable to establish the mixing and kneading condition during the production of the chewing gum as being not more than 60° C. and pH of 3.5 to 7.0 after taking the prevention of decrease in activity of the blended substance into consideration.

In addition, as merit of using the mace extract and the egg white lysozyme together, such points can be exemplified that no deficiency in taste is given by using both of them together to provide stronger effect than can be obtained in the case of using either alone, while in case of using each of them alone, a bitter taste takes place in case of more than 0.5% of mace extract, and puckery taste takes place in case of more than 3.0% of egg white lysozyme, which are unsuitable, resulting in that independent addition of mace extract or egg white lysozyme for preventing pyorrhea alveolaris has limitation and also there is limitation of effect.

As described above, it is known that lysozyme also exists in the oral cavity especially as one of enzymes of saliva and functions to destroy bacteria. In addition, it is also known that lysozyme has the anti-bacterial action as well as the anti-viral action, the hemostasis action, the anti-inflammatory action and the like. The present invention provides a chewing gum for effectively achieving prevention and restriction of pyorrhea alveolaris by using the combination of mace extract and lysozyme which has such effective function.

Mace is generally used as spices and coloring agents, the essential oil component of which contains various perfume oils having the anti-bacterial action. Generally, when usual independent spice is observed from a classification according to functional groups, there is such a tendency that the anti-bacterial action increases ester < ether < ketone < acetal < lactone < alcohol < aldehyde < acid in that order, and the mace extract contains such various compounds as the anti-bacterial components. In addition, as those for formulating as a chewing gum, mace satisfies such conditions that it has no toxicity, it has an effective activity against microorganisms, it has no taste or odor or has good taste, it can easily be used in a relatively small amount, it has good stability, it is advantageous from a view of cost and the like.

Lysozyme and the mace extract independently have effective biological activity, while they may be used together to formulate as a chewing gum for preventing pyorrhea alveolaris in certain concentrations, thereby more sufficient effect can be obtained. The use of lysozyme and the mace extract together in certain concentrations as a chewing gum for preventing pyorrhea alveolaris has been disclosed for the first time by the present invention.

According to the present invention there is provided a chewing gum which may more effectively prevent or restrict especially pyorrhea alveolaris by formulating lysozyme as a chewing gum in combination with a distinct active ingredient which satisfies such conditions that it has no toxicity, it has an effective activity against microorganisms, it has no taste or odor or has good taste, it can easily be used in a relatively small amount, it has good stability, it is advantageous from a view of cost and the like.

The present invention will be explained in detail by following examples to which the present invention is not limited.

FORMULATION OF CHEWING GUMS

Chewing gum materials were blended according to the following formulations:

TABLE 1

|                    | Ex. 1 | Ex. 2 | Ex. 3 | Comp. 1 | Comp. 2 |
|--------------------|-------|-------|-------|---------|---------|
| Gum base           | 20    | 20    | 20    | 20      | 20      |
| Sugar              | 64.5  | 64    | 64    | 64      | 65      |
| Malt honey         | 12    | 12    | 12    | 12      | 12      |
| Glycerol           | 1.7   | 1.85  | 1.7   | 2.0     | 1.7     |
| Peppermint flavor  | 1.0   | 1.0   | 1.0   | 1.0     | 1.0     |
| Mace extract       | 0.3   | 0.15  | 0.3   | —       | 0.3     |
| Egg white lysozyme | 0.5   | 1.0   | 1.0   | 1.0     | —       |
| Total              | 100.0 | 100.0 | 100.0 | 100.0   | 100.0   |

PRODUCTION OF CHEWING GUMS

Chewing gums were produced according to a usual method. For instance, the above-mentioned Japanese Patent Publication No. 49-32066 may be referred to.

METHOD OF EVALUATION

Obtained chewing gums were evaluated according to the following method of evaluation.
(1) Patients of peripheral gingivitis who were 22 to 30 years old, namely those who had been diagnosed as said patient according to visual observation, X-ray photograph and formation of gingivitis pockets, and degree of absorption of alveolar bone including 58 men and 10 women who clinically had no systematic abnormality were selected as panelists.
(2) They were subjected to chewing of chewing gums of said formulations for 5 minutes by one piece after every meal and three times a day, which was carried out for three days. During this period, no treatment for the patients was done, but habitual daily toothcleaning of each person was continued.
(3) The observation points were the upper and the lower molar tooth portions of the jaw. Observation was carried out for three weeks after initiation of the experiment with respect to the spread of pyorrhea alveolaris, the degree of pyorrhea alveolaris, the hemorrhage from tooth gums and the like, which was performed every one week in a total of 4 times.

RESULTS OF EVALUATION

The results of the clinical tests are shown as follows with respect to the hemorrhage-preventing effect from tooth gums. In addition, both in the case of the cheek side and the tongue side for each one tooth, 6 samples of liquid of the middle portion, the near portion, and the far portion were subjected to careful blotting, and after about 10 seconds percentage of the total of the portions at which hemorrhage from the pocket was observed to the tested portions was calculated to show as mean values.

TABLE 2

| Weeks passed | Ex. 1 | Ex. 2 | Ex. 3 | Comp. 1 | Comp. 2 |
|---|---|---|---|---|---|
| 0 | 28.5 | 27.6 | 28.2 | 28.5 | 26.2 |
| 1 | 19.5 | 18.7 | 15.4 | 23.5 | 23.2 |
| 2 | 16.0 | 15.3 | 10.1 | 21.7 | 21.7 |
| 3 | 12.5 | 10.8 | 5.6 | 19.7 | 18.0 |

According to the results, it is clear that the chewing gums for preventing pyorrhea alveolaris in which lysozyme of egg white and the mace extract are used together according to the present invention (Examples 1 to 3) have considerable effects as compared with those in which they are independently used (Comparative tests 1 and 2).

What is claimed is:

1. A chewing gum for preventing pyorrhea alveolaris which contains 0.2 to 3.0% by weight of lysozyme of egg white and 0.05 to 0.5% by weight of mace extract, in admixture with a gum composition comprising a gum base, sweetening agents, glycerol and a flavoring agent.

* * * * *